(12) United States Patent
Matsuo et al.

(10) Patent No.: US 10,813,392 B2
(45) Date of Patent: Oct. 27, 2020

(54) WAIST BELT

(71) Applicant: DAIYA HOLDINGS CO., LTD., Okayama (JP)

(72) Inventors: Masao Matsuo, Okayama (JP); Masayuki Kawakami, Okayama (JP)

(73) Assignee: DAIYA HOLDINGS CO., LTD., Okayama (JP)

( * ) Notice: Subject to any disclaimer, the term of this patent is extended or adjusted under 35 U.S.C. 154(b) by 78 days.

(21) Appl. No.: 16/087,158

(22) PCT Filed: Mar. 22, 2016

(86) PCT No.: PCT/JP2016/058941
§ 371 (c)(1),
(2) Date: Sep. 21, 2018

(87) PCT Pub. No.: WO2017/163303
PCT Pub. Date: Sep. 28, 2017

(65) Prior Publication Data
US 2019/0098942 A1 Apr. 4, 2019

(51) Int. Cl.
*A41D 13/05* (2006.01)
*A61F 5/02* (2006.01)
(Continued)

(52) U.S. Cl.
CPC ......... *A41D 13/0525* (2013.01); *A41D 13/05* (2013.01); *A61F 5/02* (2013.01);
(Continued)

(58) Field of Classification Search
CPC .............. A41D 13/0525; A41D 13/05; A41D 2300/32; A41D 2200/10; A41D 2400/424;
(Continued)

(56) References Cited

U.S. PATENT DOCUMENTS 5,195,948 A * 3/1993 Hill .................. A61F 5/028
602/19
5,302,171 A * 4/1994 Pearson .............. A61F 5/028
128/876

(Continued)

FOREIGN PATENT DOCUMENTS

JP  11-313846 A  11/1999
JP  2003-61993 A  3/2003
(Continued)

OTHER PUBLICATIONS

International Search Report for PCT/JP2016/058941 (dated May 31, 2016).

*Primary Examiner* — Khoa D Huynh
*Assistant Examiner* — Aiying Zhao
(74) *Attorney, Agent, or Firm* — Pearne & Gordon LLP

(57) ABSTRACT

Provided is a waist belt in which: a left inner tightening belt, with a right end portion thereof attached to the right end portion of the left body belt, is passed through the left fold ring and folded back leftward, and a left connecting ring is provided at a left end portion thereof that has passed through the right fold ring; a right inner tightening belt, with a left end portion thereof attached to the left end portion of the right body belt, is passed through the right fold ring and folded back rightward, and a right connecting ring is provided at a right end portion thereof.

1 Claim, 6 Drawing Sheets

(51) Int. Cl.
*A63B 71/12* (2006.01)
*A41F 9/02* (2006.01)

(52) U.S. Cl.
CPC ............. *A61F 5/028* (2013.01); *A63B 71/12* (2013.01); *A41D 2300/32* (2013.01); *A41F 9/02* (2013.01)

(58) Field of Classification Search
CPC .... A61F 5/02; A61F 5/028; A61F 9/02; A61F 5/022; A61F 5/03; A63B 71/12; A63B 21/00185; A63B 21/04; A63B 21/4009; A63B 2225/09; Y10T 24/4093; Y10T 24/4086; Y10T 24/4084
USPC ...................................................... 2/338, 339
See application file for complete search history.

(56) References Cited

U.S. PATENT DOCUMENTS

| | | | | |
|---|---|---|---|---|
| 5,432,951 A * | 7/1995 | Yewer, Jr. | ............... | A41F 9/002 139/384 R |
| 5,586,969 A * | 12/1996 | Yewer, Jr. | ............... | A61F 5/028 128/101.1 |
| 5,722,940 A * | 3/1998 | Gaylord, Jr. | ............ | A61F 5/028 128/96.1 |
| 6,503,215 B1 * | 1/2003 | Reinhardt | ............... | A61F 5/028 128/96.1 |
| 7,449,006 B2 * | 11/2008 | Wolanske | ............... | A61F 5/028 128/100.1 |
| 7,937,776 B1 * | 5/2011 | Anderson | ............... | A41F 9/002 2/237 |
| 8,057,417 B2 * | 11/2011 | Imai | ........................ | A61F 5/028 128/100.1 |
| 2003/0050584 A1 | 3/2003 | Toda | | |
| 2005/0177931 A1 | 8/2005 | Tsujimoto | | |
| 2014/0288474 A1 * | 9/2014 | Okada | .................... | A61F 5/024 602/19 |

FOREIGN PATENT DOCUMENTS

| | | | | |
|---|---|---|---|---|
| JP | 3094642 U | * | 7/2003 | ............... A61F 5/02 |
| JP | 2005-224509 A | | 8/2005 | |
| JP | 1490536 S | | 2/2014 | |

* cited by examiner

WAIST BELT

FIELD

The present invention relates to a waist belt that squeezes around the waist of a user.

BACKGROUND

A waist belt squeezes around the waist of a user thereof, thus reducing the risk of the user suffering or prevent the user from suffering lower back pain, or alleviating lower back pain in the user. Various structures have been proposed for a waist belt. A waist belt disclosed in Patent Literature 1 includes: a nonstretchable left body belt; a nonstretchable right body belt; a nonstretchable left inner tightening belt; a nonstretchable left outer tightening belt; a nonstretchable right inner tightening belt; and a nonstretchable right outer tightening belt. The left body belt and the right body belt are to be worn around the waist of a user by being wound around the waist of the user and having a left end portion of the left body belt and a right end portion of the right body belt connected to each other. Subsequently, the right inner tightening belt, which pulls the left body belt, is further pulled by the right outer tightening belt, and the left inner tightening belt, which pulls the right body belt, is further pulled by the left outer tightening belt, so that the left body belt and the right body belt squeezes tight around the waist of the user.

The waist belt disclosed in Patent Literature 1 has a structure in which: with a right fold ring provided in the lower half of a right end portion of the left body belt and with a left fold ring provided in the lower half of a left end portion of the right body belt, the left end portion of the left body belt and the right end portion of the right body belt are allowed to be freely connected to and disconnected from each other; the left inner tightening belt, with a right end portion thereof attached to the lower half of the right end portion of the left body belt, is passed through the left fold ring and folded back leftward, and a left connecting ring is provided at a left end portion thereof; the right inner tightening belt, with a left end portion thereof attached to the upper half of the left end portion of the right body belt, is passed through the right fold ring and folded back rightward, and a right connecting ring is provided at a right end portion thereof; the left outer tightening belt, with a right end portion thereof fixed to an outer surface of the left body belt, is pulled rightward, passed through the left connecting ring, and folded back, and a left end portion thereof is then detachably attached to the left body belt; and the right outer tightening belt, with a left end portion thereof fixed to an outer surface of the right body belt, is pulled leftward, passed through the right connecting ring, and folded back, and a right end portion thereof is then detachably attached to the right body belt.

CITATION LIST

Patent Literature

Patent Literature 1: Japanese Design Registration Publication No. 1490536

SUMMARY

Technical Problem

In the waist belt disclosed in Patent Literature 1, the right end portion of the left body belt and the left end portion of the right body belt, which face each other, each have a width (height) equal to the sum of those of the right end portion of the left inner tightening belt and the left end portion of the right inner tightening belt with the intention to avoid interference between the left inner tightening belt and the right inner tightening belt. This configuration allows, for example, the left body belt to include the right fold ring in the lower half of the right end portion thereof and to have the right end portion of the left inner tightening belt attached to the upper half of the same right end portion thereof (the same applies to the right body belt). However, this configuration results in the right end portion of the left body belt and the left end portion of the right body belt being undesirably wide although these end portions correspond to the center of the waist of the user in the rightward/leftward direction thereof. The waist belt therefore inevitably cannot squeeze around a narrow range of the waist.

If the waist belt has a double-tightening structure in which, while the right inner tightening belt pulling the left body belt is further pulled by the right outer tightening belt, the left inner tightening belt pulling the right body belt is further pulled by the left outer tightening belt, the waist belt is capable of squeezing tight around the waist of a user. However, for example, the left inner tightening belt and the left outer tightening belt are unfavorable because a direction of the squeezing diagonally crosses a direction in which the left body belt is wound around the waist of the user, which prohibits full utilization of the squeezing force of the left inner tightening belt and the left outer tightening belt for the left body belt to squeeze. The same applies to the right inner tightening belt and the right outer tightening belt.

An additional disadvantage is that force that acts to twist the left body belt and the right body belt occurs because the squeezing direction of the left inner tightening belt and the left outer tightening belt and the squeezing direction of the right inner tightening belt and the right outer tightening belt diagonally cross respective directions in which the left body belt and the right body belt are wound around the waist of the user and act for pulling in opposite directions. In consideration of this disadvantage, a narrowest possible structure has been sought out for a waist belt having a double-tightening structure that includes the left inner tightening belt and the left outer tightening belt as well as the right inner tightening belt and the right outer tightening belt, and a structure that does not generate pulling force diagonally crossing the direction in which the left body belt and the right body belt are wound around the waist of a user has been studied.

Solution to Problem

The study has resulted in development of a waist belt that includes a nonstretchable left body belt, a nonstretchable right body belt, a nonstretchable left inner tightening belt, a nonstretchable left outer tightening belt, a nonstretchable right inner tightening belt, and a nonstretchable right outer tightening belt that are arrayed in a single line. With a right fold ring provided at a right end portion of the left body belt and with a left fold ring provided at a left end portion of the right body belt, the left end portion of the left body belt and the right end portion of the right body belt are allowed to be freely connected to and disconnected from each other. The left inner tightening belt, with a right end portion thereof attached to the right end portion of the left body belt, is passed through the left fold ring and folded back leftward, and a left connecting ring is provided at a left end portion thereof that has passed through the right fold ring. The right inner tightening belt, with a left end portion thereof attached to the left end portion of the right body belt, is passed through the right fold ring and folded back rightward, and a right connecting ring is provided at a right end portion thereof. The left outer tightening belt, with a right end portion thereof fixed to an outer surface of the left body belt, is pulled rightward, passed through the left connecting ring, and folded back leftward, and a left end portion thereof is then detachably attached to the left body belt. The right outer tightening belt, with a left end portion thereof fixed to an outer surface of the right body belt, is pulled leftward, passed through the right connecting ring, and folded back rightward, and a right end portion thereof is then detachably attached to the right body belt.

Various conventionally publicly known connection/disconnection devices are usable as a connection/disconnection device for connecting and disconnecting the left end portion of the left body belt and the right end portion of the right body belt to and from each other. Preferably, the connection/disconnection device is composed of a male surface and a female surface of a hook-and-loop fastener being assigned to the left end portion of the left body belt and the right end portion of the right body belt, respectively. Likewise, various conventionally publicly known attachment/detachment devices are usable as an attachment/detachment device for attaching and detaching the left outer tightening belt to and from the left body belt and as an attachment/detachment device for attaching and detaching the right outer tightening belt to and from the right body belt. Preferably, each of the attachment/detachment devices is composed of a male surface and a female surface of a hook-and-loop fastener being assigned to an outer surface of the left body belt or the right body belt and the inner surface of a left end portion of the left outer tightening belt or an inner surface of a right end portion of the right outer tightening belt.

A waist belt according to the present invention includes a nonstretchable left body belt, a nonstretchable right body belt, a nonstretchable left inner tightening belt, a nonstretchable left outer tightening belt, a nonstretchable right inner tightening belt, and a nonstretchable right outer tightening belt that are arrayed in a single line. The left inner tightening belt and the right inner tightening belt are prevented from interfering with each other in a manner such that the left inner tightening belt is passed through the left fold ring, folded back leftward, and then passed through the right fold ring. The left inner tightening belt and the right inner tightening belt can be prevented from interfering with each other in a manner such that one of the left inner tightening belt and the right inner tightening belt is passed through the right fold ring or the left fold ring of the other one of the left and the right inner tightening belts. Hereinafter, possible structures of the waist belt according to the present invention include one having the right inner tightening belt passed through the right fold ring, folded back rightward, and then passed through the left fold ring instead of the one having the left inner tightening belt passed through the left fold ring and folded back leftward, and then passed through the right fold ring.

"Left", "right", "up", and "down" in the present invention refer to "left", "right", "up", and "down" with respect to a user when the user has the waist belt on, and agree with "left", "right", "up", and "down" in the back-side development view of the waist belt and "left", "right", "up", and "down" of a structure thereof. Likewise, "inner" refers to a side that makes contact with the user while "outer" refers to a side that can be viewed from the outside. "Left half", "right half", "upper half", and "lower half" refer to parts obtained by halving the left body belt, the right body belt, the left tightening belt, the left inner tightening belt, the left outer tightening belt, the right tightening belt, the right inner tightening belt, the right outer tightening belt, a left subsidiary tightening belt, or a right subsidiary tightening belt in a rightward/leftward direction or in an upward/downward direction thereof; specifically, "left half" signifies a left part obtained by the halving into right and left parts, "right half" signifies a right part obtained by the halving into right and left parts, "upper half" signifies an upper part obtained by the halving into upper and lower parts, and "lower half" signifies a lower part obtained by the halving into upper and lower parts.

Each of the "left fold ring", the "right fold ring", the "left connecting ring", and the "right connecting ring" in the present invention is an annular member made of resin or metal such as an oval jumpring or an adjuster buckle. It is preferable that each of the "left fold ring", the "right fold ring", the "left connecting ring", and the "right connecting ring" be completely closed. However, each of the "left fold ring", the "right fold ring", the "left connecting ring", and the "right connecting ring" may have a gap that is small enough to keep corresponding one of the left inner tightening belt, the left outer tightening belt, the right inner tightening belt, and the right outer tightening belt from slipping out therefrom, the one having been brought therethrough to be wound around.

Advantageous Effects of Invention

The waist belt of the present invention has a narrower width and is thus capable of squeezing around the waist of a user in a narrower range than a conventional one despite having a double-tightening structure that includes the left inner tightening belt and the left outer tightening belt as well as the right inner tightening belt and the right outer tightening belt. This advantageous effect is produced by having the left body belt, the right body belt, the left inner tightening belt, the left outer tightening belt, the right inner tightening belt, and the right outer tightening belt arrayed in a single line as a result of having the left inner tightening belt passed through the left fold ring, folded back leftward, and then passed through the right fold ring so that the left inner tightening belt and the right inner tightening belt can be prevented from interfering with each other.

By having the left body belt, the right body belt, the left inner tightening belt, the left outer tightening belt, the right inner tightening belt, and the right outer tightening belt arrayed in a single line, another advantageous effect can also be produced such that: the squeezing directions of the left inner tightening belt, the left outer tightening belt, the right inner tightening belt, and the right outer tightening belt consequently agree with the directions in which the left body belt and the right body belt are wound around the waist of a user, which enables full utilization of the squeezing force of the left inner tightening belt, the left outer tightening belt, the right inner tightening belt, and the right outer tightening belt without the left body belt and the right body belt twisted, for example.

DESCRIPTION OF EMBODIMENTS

Figure 1:
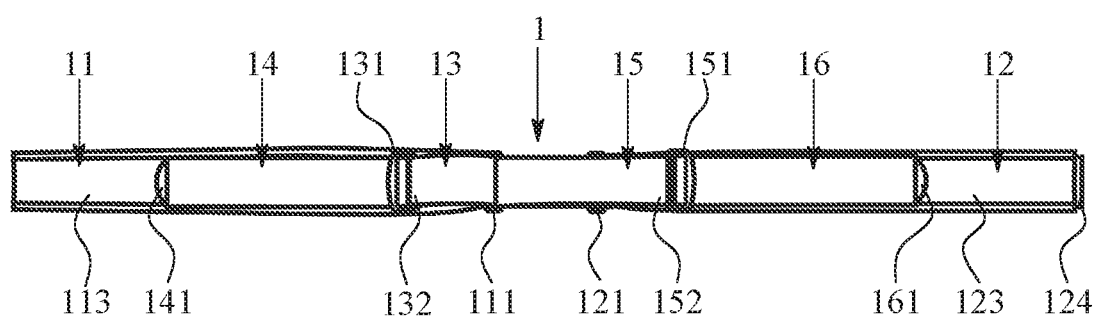
FIG. 1 is a front view of an example of a waist belt to which the present invention is applied.
Figure 2:
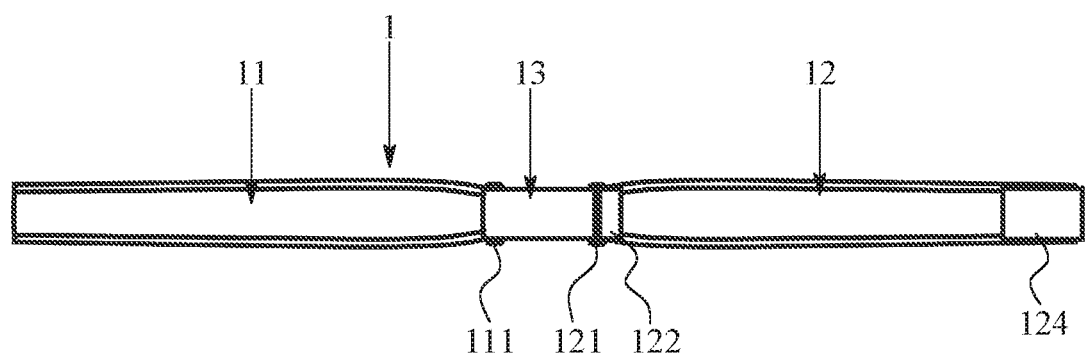
FIG. 2 is a back view of the waist belt given as the example.
Figure 3:
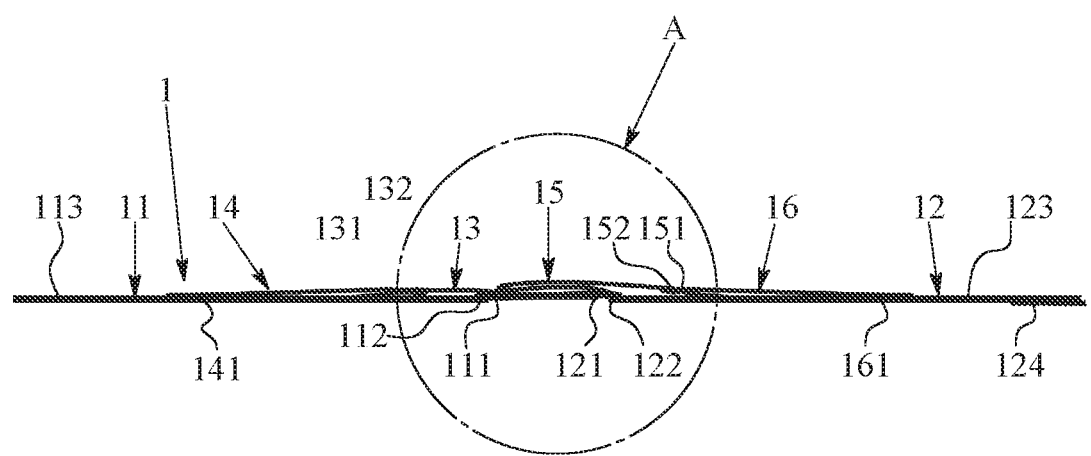
FIG. 3 is a bottom view of the waist belt given as the example.
Figure 4:
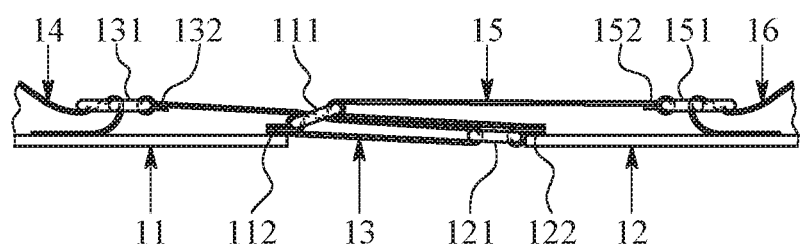
FIG. 4 is an enlarged bottom view of the part A of FIG. 3.

The following describes an embodiment for carrying out the present invention with reference to the drawings. As illustrated in FIG. 1 to FIG. 4, for example, a waist belt 1 according to the present invention includes a nonstretchable left body belt 11, a nonstretchable right body belt 12, a nonstretchable left inner tightening belt 13, a nonstretchable left outer tightening belt 14, a nonstretchable right inner tightening belt 15, and a nonstretchable right outer tightening belt 16 that are arrayed in a single line. The waist belt 1 of this example is capable of squeezing around a waist 21 of a user 2 (see FIG. 6 described later) with a narrower width than a conventional waist belt of the same type (see Patent Literature 1), that is, a type having a double-tightening structure with the left body belt 11, the right body belt 12, the left inner tightening belt 13, the left outer tightening belt 14, the right inner tightening belt 15, and the right outer tightening belt 16 configured to have the same width (height).

The left body belt 11 of this example is a lengthened nonstrechable belt constituting the left half of the waist belt 1 and has a right fold ring 111 provided to a right end portion thereof by means of a flap attached to ring 112 sewn onto a short side thereof at the right end portion. The right fold ring 111 of this example is an oval jumpring that is an annular ring having a substantially rectangular outer shape and made of resin or metal, which is connected by having one of the paired long sides thereof passed through a loop portion of the flap attached to ring 112. To the left body belt 11 of this example, an female surface of hook and loop fastener for attachment/detachment 113, which is paired with a male surface of hook and loop fastener for connection 124 of the right body belt 12 and an male surface of hook and loop fastener for attachment/detachment 141 of the left outer tightening belt 14, is provided on the outer surface side thereof in a range from a left end portion to a center portion thereof.

The right body belt 12 of this example is a nonstrechable belt constituting the right half of the waist belt 1 and has a left fold ring 121 provided to a left end portion thereof by means of a flap attached to ring 122 sewn onto a short side thereof at the left end portion. The left fold ring 121 of this example is an oval jumpring that is an annular ring having a substantially rectangular outer shape and made of resin or metal, which is connected by having one of the paired long sides thereof passed through a loop portion of the flap attached to ring 122. To the right body belt 12 of this example, an female surface of hook and loop fastener for attachment/detachment 123, which is paired with an male surface of hook and loop fastener for attachment/detachment 161 of the right outer tightening belt 16, is provided on the outer surface side thereof in a range from the right end portion to a center portion thereof. To the right body belt 12 of this example, the male surface of hook and loop fastener for connection 124, which is paired with the female surface of hook and loop fastener for attachment/detachment 113 provided on the outer surface of the left body belt 11, is provided on the inner surface side of a flap sewn onto the inner side of the right end portion thereof.

While being sandwiched between the flap attached to ring 112 and a right end portion of the left body belt 11, the left inner tightening belt 13 of this example has a right end portion thereof sewn onto the right end portion of the left body belt 11. The left inner tightening belt 13 of this example is used in a manner such that, after a left end portion thereof is pulled rightward, the left inner tightening belt 13 is put around the remaining one of the long sides of the left fold ring 121 of the right body belt 12 from the inner side (the lower side in FIG. 3) and folded back leftward. The left inner tightening belt 13 of this example has a left connecting ring 131 provided at the left end portion thereof, which is projected from the right fold ring 111 of the left body belt 11 after the left inner tightening belt 13 is brought therethrough. The left connecting ring 131 is an adjuster buckle that is an annular ring made of resin or metal that has a substantially rectangular outer shape and includes an center bar parallel to and between the paired long sides of the left connecting ring 131. The left connecting ring 131 is connected by having one of the long sides thereof passed through a end portion for attaching ring 132 provided at the left end portion of the left inner tightening belt 13 and having a loop shape.

The left outer tightening belt 14 of this example has a right end portion thereof sewn onto the outer surface of the left body belt 11, thereby being fixed thereto. After a left end portion of the left outer tightening belt 14 is pulled rightward and passed through the left connecting ring 131 provided at the left end portion of the left inner tightening belt 13, the left outer tightening belt 14 is folded back leftward and detachably attached, by means of the male surface of hook and loop fastener for attachment/detachment 141 provided at the left end portion thereof, to the female surface of hook and loop fastener for attachment/detachment 113 provided on the outer surface of the left body belt 11. Because the left connecting ring 131 of this example is an adjuster buckle, the left end portion of the left outer tightening belt 14 is projected toward the outside from the inside (the lower side in FIG. 3) through a part on the right with respect to the center bar, is then folded back to be projected toward the inside through a part on the left with respect to the center bar, and is then pulled out leftward while being attached to the remaining one of the long sides of the left connecting ring 131 from the inside. Thus, slacking of the left outer tightening belt 14 put through and around the left connecting ring 131, which is an adjuster buckle, is prevented.

The right inner tightening belt 15 of this example has a left end portion thereof sewn onto the flap attached to ring 122 sewn onto the left end portion of the right body belt 12. The right inner tightening belt 15 of this example, after a right end portion thereof is pulled leftward, is put around the remaining one of the long sides of the right fold ring 111 of the left body belt 11 from the inside (the lower side in FIG. 3) and folded back leftward. In this state, the left inner tightening belt 13 passed through the right fold ring 111 is located inside with respect to the right inner tightening belt 15 passed through the right fold ring 111. The right inner tightening belt 15 of this example has a right connecting ring 151 provided at the right end portion thereof, which is projected rightward. The right connecting ring 151 is an adjuster buckle that is an annular ring made of resin or metal that has a substantially rectangular outer shape and includes an center bar parallel to and between the paired long sides of the right connecting ring 151. The right connecting ring 151 is connected by having one of the long sides thereof passed through a end portion for attaching ring 152 provided at the right end portion of the right inner tightening belt 15 and having a loop shape.

The right outer tightening belt 16 of this example has a left end portion thereof sewn onto the outer surface of the right body belt 12, thereby being fixed thereto. After a right end portion of the right outer tightening belt 16 is pulled leftward and passed through the right connecting ring 151 provided at the right end portion of the right inner tightening belt 15, the right outer tightening belt 16 is folded back rightward and detachably attached, by means of the male surface of hook and loop fastener for attachment/detachment 161 provided at the right end portion thereof, to the female surface of hook and loop fastener for attachment/detachment 113 provided on the outer surface of the right body belt 12. Because the right connecting ring 151 of this example is an adjuster buckle, the right end portion of the right outer tightening belt 16 is projected toward the outside from the inside (the lower side in FIG. 3) through a part on the left with respect to the center bar, is then folded back to be projected toward the inside through a part on the right with respect to the center bar, and is then pulled out rightward while being attached to the remaining one of the long sides of the right connecting ring 151 from the inside. Thus, slacking of the right outer tightening belt 16 put through and around the right connecting ring 151, which is an adjuster buckle, is prevented.

The waist belt 1 of this example is worn on the waist 21 of the user 2 through the following procedure. The left body belt 11 and the right body belt 12 are disconnected from each other by having the male surface of hook and loop fastener for connection 124 of the right body belt 12 separated from the female surface of hook and loop fastener for attachment/detachment 113 provided on the outer surface of the left body belt 11. In the left outer tightening belt 14, the male surface of hook and loop fastener for attachment/detachment 141 is separated from the female surface of hook and loop fastener for attachment/detachment 113 provided on the outer surface of the left body belt 11, so that the left inner tightening belt 13 and the left outer tightening belt 14 are set free. Likewise, in the right outer tightening belt 16, the male surface of hook and loop fastener for attachment/detachment 161 is separated from the female surface of hook and loop fastener for attachment/detachment 123 provided on the outer surface of the right body belt 12, so that the right inner tightening belt 15 and the right outer tightening belt 16 are set free. Preparation is thus completed.

After the preparation is completed, the waist belt 1 is handled in a manner such that: the insides of the left body belt 11 and the right body belt 12 are attached to the waist 21 of the user 2; and the left end portion of the left body belt 11 and the right end portion of the right body belt 12 are put over the belly. Subsequently, the waist belt 1 is handled in a manner such that: the left body belt 11 and the right body belt 12 are overlapped on each other while being placed inside and outside, respectively; and the female surface of hook and loop fastener for attachment/detachment 113 provided on the outer surface of the left body belt 11 is hooked to the male surface of hook and loop fastener for connection 124 provided at the right end portion of the right body belt 12, so that the left body belt 11 and the right body belt 12 are connected to each other. Thus, the waist belt 1 is brought to a state loosely wound around the waist 21 of the user 2.

Figure 5:
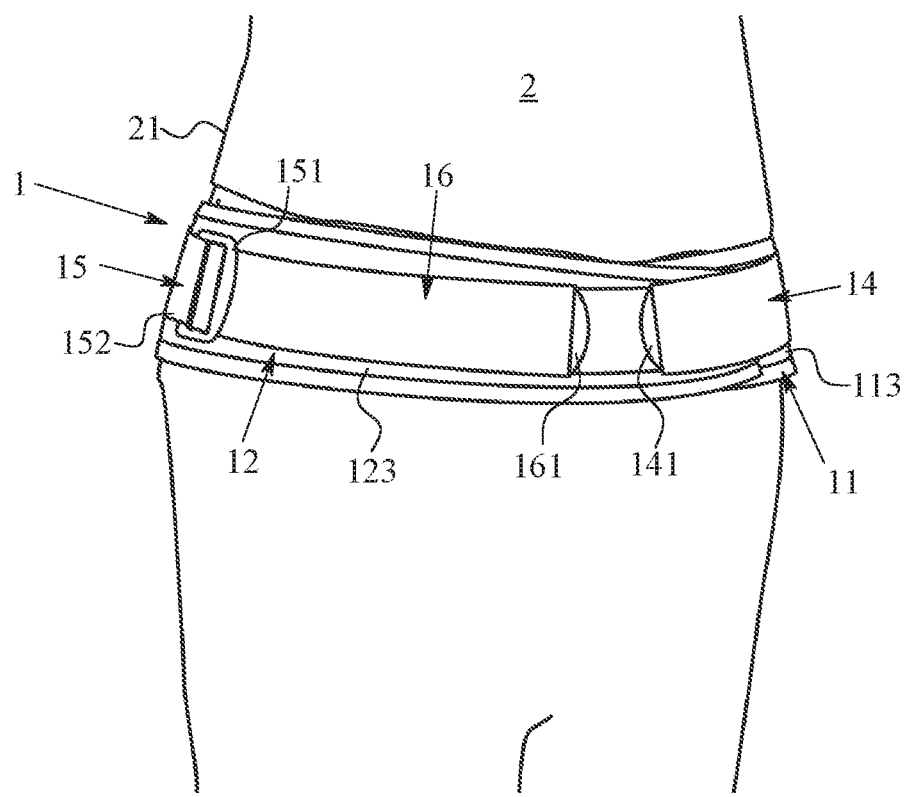
FIG. 5 is a front-side perspective view of the waist belt given as the example in a worn state.
Figure 6:
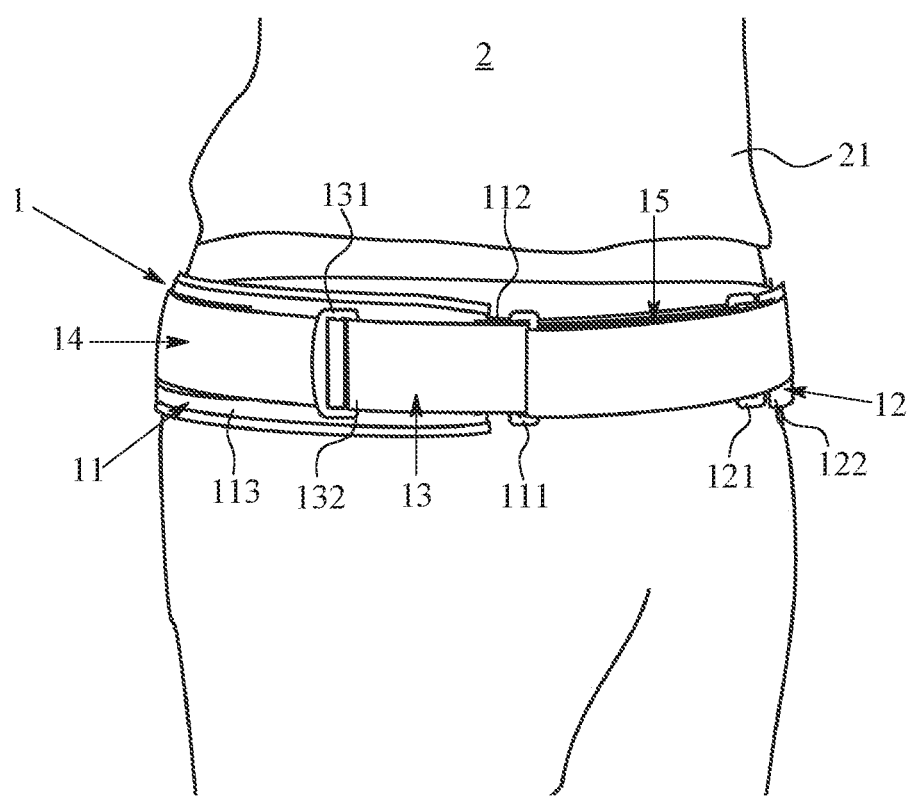
FIG. 6 is a back-side perspective view of the waist belt given as the example in a worn state.

After being loosely wound around the waist 21 of the user 2, the waist belt 1 is handled in a manner such that the left outer tightening belt 14 and the right outer tightening belt 16 are tightened individually. The left outer tightening belt 14 is pulled to be wound around leftward with the left end portion thereof gripped and is secured by having the male surface of hook and loop fastener for attachment/detachment 141 at the left end portion thereof hooked to the female surface of hook and loop fastener for attachment/detachment 113 provided on the outer surface of the left body belt 11. Likewise, with the user 2 viewed from above, the right outer tightening belt 16 is pulled to be wound around rightward with the right end portion thereof gripped and is secured by having the male surface of hook and loop fastener for attachment/detachment 161 at the right end portion thereof hooked to the female surface of hook and loop fastener for attachment/detachment 123 provided on the outer surface of the right body belt 12. Thus, the waist belt 1 is worn on the waist 21 of the user 2 as illustrated in FIG. 5 and FIG. 6.

For example, the left outer tightening belt 14 pulls the left end portion of the left inner tightening belt 13 via the left connecting ring 131, and the left inner tightening belt 13 pulls the right body belt 12 via the left fold ring 121. Force that pulls the left end portion of the right body belt 12 is divided into force from the left end portion of the left inner tightening belt 13 and force from the right end portion thereof, and force that pulls the left end portion of the left inner tightening belt 13 is divided into force from the left end portion of the left outer tightening belt 14 and force from the right end portion thereof. Therefore, when pulling the left end portion of the left outer tightening belt 14, the user 2 only needs to apply one-quarter of the force that pulls the left end portion of the right body belt 12. Likewise, when pulling the right end portion of the right outer tightening belt 16, the user 2 only needs to apply one-quarter of force that pulls the right end portion of the left body belt 11.

The user 2 is allowed to cause the left body belt 11 and the right body belt 12 to squeeze tight around the waist 21 of the user 2 while pulling the left outer tightening belt 14 and the right outer tightening belt 16 with a weak force. As already described, the left body belt 11, the right body belt 12, the left inner tightening belt 13, the left outer tightening belt 14, the right inner tightening belt 15, and the right outer tightening belt 16 are arrayed in a single line, whereby the left body belt 11 and the right body belt 12 are not twisted when the left inner tightening belt 13, the left outer tightening belt 14, the right inner tightening belt 15, and the right outer tightening belt 16 are tightened. Furthermore, directions in which the left body belt 11 and the right body belt 12 are wound around the waist 21 of the user 2 agree with directions of squeezing by the left inner tightening belt 13, the left outer tightening belt 14, the right inner tightening belt 15, and the right outer tightening belt 16, whereby the directions of squeezing can be easily adjusted with reference to the directions in which the left body belt 11 and the right body belt 12 are wound.

REFERENCE SIGNS LIST 1 waist belt
11 left body belt
111 right fold ring
112 flap attached to ring
113 female surface of hook and loop fastener for attachment/detachment
12 right body belt
121 left fold ring
122 flap attached to ring
123 female surface of hook and loop fastener for attachment/detachment
124 male surface of hook and loop fastener for connection 13 left inner tightening belt
131 left connecting ring
132 end portion for attaching ring
14 left outer tightening belt
141 male surface of hook and loop fastener for attachment/detachment
15 right inner tightening belt
151 right connecting ring
152 end portion for attaching ring
16 right outer tightening belt
161 male surface of hook and loop fastener for attachment/detachment
2 user
21 waist

The invention claimed is:

1. A waist belt comprising:
a nonstretchable left body belt;
a nonstretchable right body belt;
a nonstretchable left inner tightening belt;
a nonstretchable left outer tightening belt;
a nonstretchable right inner tightening belt; and
a nonstretchable right outer tightening belt,
wherein the left body belt, the right body belt, the left inner tightening belt, the left outer tightening belt, the right inner tightening belt, and the right outer tightening belt are arrayed in a single line extending along the waist belt,
with a right fold ring provided at a right end portion of the left body belt and with a left fold ring provided at a left end portion of the right body belt, a left end portion of the left body belt and a right end portion of the right body belt are allowed to be freely connected to and disconnected from each other,
the left inner tightening belt, with a right end portion of the left inner tightening belt attached to the right end portion of the left body belt, is passed through the left fold ring and folded back leftward, and the left inner tightening belt is inserted into the right fold ring, and a left connecting ring is provided at a left end portion of the left inner tightening belt,
the right inner tightening belt, with a left end portion of the right inner tightening belt attached to the left end portion of the right body belt, is passed through the right fold ring and folded back rightward, and a right connecting ring is provided at a right end portion of the right inner tightening belt,
the left outer tightening belt, with a right end portion of the left outer tightening belt fixed to an outer surface of the left body belt, is pulled rightward by a user when the waist be is worn, passed through the left connecting ring, and folded back leftward, and a left end portion of the left outer tightening belt is then detachably attached to the left body belt, and
the right outer tightening belt, with a left end portion of the right outer tightening belt fixed to an outer surface of the right body belt, is pulled leftward by the user when the waist belt is worn, passed through the right connecting ring, and folded back rightward, and a right end portion of the right outer tightening belt is then detachably attached to the right body belt.

* * * * *

UNITED STATES PATENT AND TRADEMARK OFFICE
CERTIFICATE OF CORRECTION

Page 1 of 1

PATENT NO. : 10,813,392 B2
APPLICATION NO. : 16/087158
DATED : October 27, 2020
INVENTOR(S) : Masao Matsuo and Masayuki Kawakami It is certified that error appears in the above-identified patent and that said Letters Patent is hereby corrected as shown below:

In the Claims

Column 10, Line 19, Claim 1: "the waist be is worn," should read -- the waist belt is worn, --

Signed and Sealed this
Sixteenth Day of February, 2021

Drew Hirshfeld
*Performing the Functions and Duties of the*
*Under Secretary of Commerce for Intellectual Property and*
*Director of the United States Patent and Trademark Office*